United States Patent [19]

Schenk et al.

[11] 4,284,576
[45] Aug. 18, 1981

[54] PREPARATION OF ANTHRAQUINONE FROM TETRAHYDROANTHRAQUINONE

[75] Inventors: Norbert Schenk, Leverkusen; Jörg Krekel, Essen; Paul Losacker, Leichlingen; Wolfgang Swodenk, Odenthal-Gloebusch, all of Fed. Rep. of Germany

[73] Assignee: Bayer Aktiengesellschaft, Leverkusen, Fed. Rep. of Germany

[21] Appl. No.: 944,934

[22] Filed: Sep. 22, 1978

Related U.S. Application Data

[63] Continuation of Ser. No. 822,011, Aug. 4, 1977, abandoned, which is a continuation of Ser. No. 706,091, Jul. 16, 1976, abandoned.

[30] Foreign Application Priority Data

Jul. 19, 1975 [DE] Fed. Rep. of Germany ....... 2532398

[51] Int. Cl.$^3$ ............................................. C07C 50/18
[52] U.S. Cl. .................................................... 260/369
[58] Field of Search ........................................ 260/369

[56] References Cited

U.S. PATENT DOCUMENTS

| | | | |
|---|---|---|---|
| 1,114,843 | 10/1914 | Wright | 23/263 X |
| 2,839,369 | 6/1958 | Mulllins | 23/263 |
| 3,062,616 | 11/1962 | Chadwick | 23/263 X |
| 3,870,730 | 3/1975 | Scharfe et al. | 260/369 |

OTHER PUBLICATIONS

Kirschbaum, "Distillation & Rectification", Chem. Pub. Co. Inc., N.Y. 1948, TP/156/D5k5, pp. 120, 154–156.

*Primary Examiner*—Patrick Garvin
*Assistant Examiner*—Raymond K. Covington
*Attorney, Agent, or Firm*—Sprung, Felfe, Horn, Lynch & Kramer

[57] ABSTRACT

In the preparation of anthraquinone by reacting a mixture containing naphthalene, phthalic anhydride and tetrahydroanthraquinone with oxygen at elevated temperature while simultaneously separating off at least part of the naphthalene, the improvement which comprises supplying the naphthalene, phthalic anhydride and tetrahydroanthraquinone to a distillation system which consists of a column having a rectifying section, a stripping section and a boiler, at least one of the stripping section and the boiler being designed so that rapid through-passage of the feed mixture is prevented. Downcomers in the stripping section maintain liquid levels on the trays of about 5 to 500 mm and the boiler may have several successive chambers to provide the desired residence time in the system. A liquid mixture of naphthalene, phthalic anhydride and anthraquinone is removed from the boiler while a gas mixture including naphthalene is taken off from the rectifying section, being cooled to condense naphthalene for use in oxidation to naphthoquinone and phthalic anhydride.

12 Claims, No Drawings

PREPARATION OF ANTHRAQUINONE FROM TETRAHYDROANTHRAQUINONE

This application is a continuation of Ser. No. 822,011 filed Aug. 4, 1977 and now abandoned, which is a continuation of Ser. No. 706,091, filed July 16, 1976 and now abandoned.

A quite recent synthesis for anthraquinone consists in first preparing naphthoquinone, starting from naphthalene, reacting this naphthoquinone in Diels-Alder reaction with butadiene to give tetrahydroanthraquinone and then obtaining anthraquinone therefrom by reaction with oxygen or gases containing oxygen. Such processes are described, for example, in U.S. Pat. Nos. 2,938,913 and 3,870,730, the disclosures of which are incorporated herein by reference. The present invention relates to a particularly advantageous process for carrying out the final stage of this anthraquinone synthesis.

In the process according to U.S. Pat. No. 2,938,913, the mixture which is present after the Diels-Alder reaction and which contains tetrahydroanthraquinone, solvent and naphthalene is first treated with aqueous alkali, an aqueous alkaline solution of salts of tetrahydroanthraquinone and a mixture of solvent and naphthalene being obtained. Crude solid anthraquinone is isolated from the solution containing the salts of tetrahydroanthraquinone by passing air through this solution and filtering off the anthraquinone which precipitates out. The mixture of naphthalene and the solvent is separated, by distillation, into the components, which can then be re-used in the anthraquinone synthesis.

This process has a number of disadvantages. Thus, because anthraquinone precipitates out during the final stage and because of the danger of blockage associated therewith, it can be carried out continuously only with difficulty. In addition, because of the use of dilute solution, large reaction apparatuses are necessary. The aqueous alkaline solution is a solvent which is foreign to the system and the preparation, purification and recycling of which require additional effort.

According to the process of U.S. Pat. No. 3,870,730, a liquid mixture which contains naphthalene, phthalic anhydride and tetrahydroanthraquinone is present after the Diels-Alder reaction and, where appropriate, after excess butadiene has been separated off. The further processing of this mixture can then be carried out in various ways. According to one variant, naphthalene can first be removed by distillation in a column and the remaining liquid residue, optionally after the addition of additional phthalic anhydride, made to react with oxygen or gases containing oxygen, for example in a bubble column. With this procedure some of the phthalic anhydride is withdrawn in the gas form from the bubble column and this necessitates the use of devices for isolating and, optionally, recycling this phthalic anhydride. According to another variant, a gas containing oxygen can be passed into the distillation for the removal of naphthalene and a partial or complete conversion of the tetrahydroanthraquinone present into anthraquinone can thus be carried out in this distillation column. A mixture which essentially contains phthalic anhydride, anthraquinone and tetrahydroanthraquinone, or phthalic anhydride and anthraquinone, can then be withdrawn from the sump of the column. If the sump product still contains tetrahydroanthraquinone, this can be partly converted, or completely converted, to anthraquinone, for example in a downstream bubble column. A gas which contains naphthalene and is substantially free from phthalic anhydride can be taken off at the top of the column.

This process is considerably more advantageous than the process according to U.S. Pat. No. 2,938,913 and can give good results. In view of the requisite expenditure on apparatus, the most advantageous embodiment of this process is to carry out the conversion of tetrahydroanthraquinone to anthraquinone in the column used for separating off naphthalene, since, in this case, a saving can be made in respect of a separate device for this reaction, for example a bubble column. It has been found that, compared with the other embodiments, this embodiment, which is the most advantageous with regard to the requisite expenditure on apparatus, in some cases gives less good results in respect of selectivity and yield.

The object of the present invention is therefore, to provide a process by which, starting from a mixture which essentially contains naphthalene, phthalic anhydride and tetrahydroanthraquinone, it is possible, in one apparatus, at least partially to separate off napthalene and to convert tatrahydroanthraquinone to anthraquinone with good selectivity and in good yield.

A process for the preparation of anthraquinone by reacting a mixture which essentially contains naphthalene, phthalic anhydride and tetrahydroanthraquinone with oxygen at elevated temperature and while simultaneously separating off at least part of the naphthalene has now been found which is characterized in that a distillation system which consists of a column having a rectifying section and a stripping section and of a boiler and in which the stripping section and/or the boiler is of such design that rapid through-passage of the feed mixture is prevented, is used.

In the process according to the invention, the composition of the feed material, which essentially contains naphthalene, phthalic anhydride and tetrahydroanthraquinone, can vary within wide limits. For example, the feed mixture can contain about 10 to 95% by weight of naphthalene, about 5 to 90% by weight of phthalic anhydride and about 3 to 30% by weight of tetrahydroanthraquinone. Feed mixtures which contain about 50 to 90% by weight of naphthalene, about 15 to 50% by weight of phthalic anhydride and about 5 to 15% by weight of tetrahydroanthraquinone are preferred. In addition to these constituents, the feed material can also contain smaller amounts, for example about 1 to 5% by weight of other substances. Such other substances can be, for example, high-boiling compounds, butadiene, vinylcyclohexene, naphthoquinone, naphthohydroquinone, naphthacenquinone and/or phthalic acid.

Suitable feed materials for the process according to the invention can be obtained, for example, by oxidizing naphthalene in the gas phase, isolating a mixture of naphthoquinone, phthalic anhydride and naphthalene from the reaction products, reacting this mixture with butadiene in a Diels-Alder reaction, in which tetrahydroanthraquinone is formed from naphthoquinone, and removing any excess butadiene which may be present (compare, for example, U.S. Pat. No. 3,870,730. The composition of the mixture thus obtained can be changed, before it is fed into the process according to the invention, by, for example, adding naphthalene and/or phthalic anhydride in pure form or in the form of mixtures to the feed mixture. In particular, it can be advantageous to add phthalic anhydride which is obtained within the framework of the anthraquinone synthesis, during the purification of anthraquinone, to the mixture obtained from the Diels-Alder reaction, after excess butadiene has been separated off. It is also possible to introduce naphthalene and/or phthalic anhydride prior to the Diels-Alder reaction, for example into the butadiene which is to be added at that point.

The oxygen required in the process according to the invention can be employed as such or as a mixture with other gases, for example as a mixture with nitrogen, carbon dioxide, steam and/or naphthalene. It is advantageous to employ the oxygen as a mixture with other gases and the oxygen content of such mixtures can be, for example, about 1 to 10, and preferably about 5 to 8,% by volume. Oxygen-containing gas mixtures which are obtained within the framework of the anthraquinone synthesis during the oxidation of naphthalene to naphthoquinone and after separating off phthalic anhydride, naphthoquinone and, optionally, naphthalene are particularly preferentially employed. Such gas mixtures can contain, for example, about 7 to 9% by volume of oxygen, about 60 to 90% by volume of nitrogen, about 0.5 to 10% by volume of carbon dioxide, about 0.3 to 3% by volume of carbon monoxide, about 5 to 15% by volume of steam and about 1 to 5% by volume of naphthalene. The quantity of oxygen or of the gas mixture containing oxygen can be varied within wide limits. Advantageously, an excess of oxygen, for example about 1.3 to 50 times the amount, based on the stoichiometric amount for the conversion of tetrahydroanthraquinone to anthraquinone, is used.

A distillation system which consists of a column, with a rectifying section and a stripping section, and a boiler is used for the process according to the invention.

The rectifying section of the column can be of any desired design and has, for example, about 2 to 20, and preferably about 5 to 10, theoretical plates. The rectifying section can contain packing of any desired shape, sieve trays, bubble cap trays, valve trays or drip trays.

According to the invention, the stripping section of the column and/or the boiler of the distillation system is of such design that rapid through-passage of the feed mixture is prevented. In general, it is necessary only that either the stripping section or the boiler is designed in a special way. However, it is also possible for the stripping section and the boiler to be of special design.

Rapid through-passage of the feed mixture through the stripping section of the column can be prevented, according to the invention, by using a stripping section which has special inserts. Inserts which can be used are, for example, sieve trays, bubble cap trays, valve trays or drip trays which are connected to one another by downcomers and act as a reaction cascade. The downcomers can be arranged in such a way that overflow weirs of between about 5 and 500 mm, preferably between about 30 and 150 mm, result on the individual trays. The stripping section preferably contains about 5 to 20 trays. The liquid load can be determined by the reflux, in the customary manner. It can also be increased at specific points in the column, for example by supplying a liquid, for instance phthalic anhydride, or by a special internal circulation of liquid. When the stripping section of the column contains special inserts, the boiler of the column can be designed in any desired way, for example as a sump boiler.

Rapid through-passage of the feed mixture through the boiler of the distillation system can be prevented, according to the invention, by using a boiler which consists of several chambers and is operated as a reaction cascade.

The number of chambers can be, for example, about 2 to 5 and preferably about 2 to 4. The individual chambers can be arranged one above the other. In this case, the individual chambers can be separated by sieve trays and the mixture can pass through in co-current. It is also possible for the individual chambers to be arranged in parallel and for all or some of the chambers to be located upstream of the column. In this case, the individual chambers can consist, for example, of separate kettles which are arranged in the form of a kettle cascade. When the individual chambers are arranged in parallel or are arranged in the form of a kettle cascade, the final kettle or the final chamber is preferably the sump of the column. The rate at which the liquid flows through the chambers is appropriately so selected that minimal back-mixing takes place. When the boiler of the distillation system consists of several chambers, the stripping section of the column can be designed in any desired way, that is to say, for example, without the special inserts previously mentioned and in particular without the overflow weirs.

Heat can be supplied to the boiler, independently of the design of the latter. The supply of heat can be effected, for exampl through the walls, by means of fitted heat exchange tubes or by means of a circulation evaporator, with or without forced circulation, which is connected to the boiler.

The mixture containing naphthalene, phthalic anhydride and tetrahydroanthraquinone is appropriately fed in in the liquid form, either between the upper region of the stripping section and the lower region of the rectifying section of the column or into the boiler. The entire liquid feed stream can be fed in at one point. However, it is also possible to divide the liquid feed stream into several partial streams and to feed these in at different points, for example in the rectifying section or in the boiler. When a boiler consisting of several chambers is used, it is advantageous to pass the liquid feed mixture into the first chamber. In addition a stream of phthalic anhydride can be fed into the column.

Addition of the oxygen or of the gas containing oxygen is effected in the lower region of the distillation system, appropriately in the lower region of the stripping section of the column or in the boiler. When the boiler consists of several chambers, the addition can be made into one or more of these chambers. The gas is advantageously introduced into the distillation system via a distribution device, for example through frit trays, bubble cap trays, sieve trays or valve trays or through nozzles. Nozzles, especially two-component nozzles, are preferably used.

It is advantageous to introduce the gas into the distillation system through one or more two-component nozzles and in this case a stream of liquid is optionally withdrawn from the distillation system and, for warming, fed through a heat exchanger and this stream is fed as the second component to the two-component nozzle. This stream of liquid can, for example, be in an amount such that about 3 to 200 kg of liquid per $m^3_{actual}$ of gas are fed to a two-component nozzle. Preferably, about 10 to 50 kg per $m^3_{actual}$ of gas are fed to a two-component nozzle. (The expression "$m^3_{actual}$" refers to the volume of gas in cubic meters as measured under operating conditions, and not under standard conditions).

A liquid mixture, which essentially contains phthalic anhydride, anthraquinone and naphthalene and which can contain smaller amounts of high-boiling compounds and by-products, is withdrawn from the sump of the column or from the boiler and, in the case of a boiler which consists of several chambers, preferably from the final chamber. Pure anthraquinone can be isolated from this mixture in any desired manner, for example by means of a multi-stage distillation.

A stream of gas, which contains the unreacted proportions of the oxygen, or gas containing oxygen, fed into the lower part of the distillation system and also naphthalene and, in some cases, low-boiling compounds, is taken off at the top of the column. This stream of gas can be worked up in various ways. For example, the stream of gas can be fed to an off-gas purification unit, for example to a unit for catalytic purification or combustion, and in this way an off-gas which can be withdrawn from the system can be obtained. It is, however, advantageous to isolate the organic constituents, especially the naphthalene, from this stream of gas. For this purpose, the stream of gas can be subjected, for example to cooling. The stream of gas can be fed, for example, to two coolers, which are operated as alternating coolers and can be cooled, for example, with water at about 10° to 40° C., and, in every case, the organic constituents of the gas, especially naphthalene, are deposited in the solid form in one cooler and the solid precipitate is melted off in the other cooler. All or part of the liquid which is thus obtainable and consists mainly of naphthalene can be recycled, as reflux, to the top of the column and/or all or part of the said liquid can be recycled to another point in the anthraquinone synthesis, for example into the feed product for the Diels-Adder reaction or into the feed product for the distillation system to be used according to the invention.

Particularly preferentially, the stream of gas taken off at the top of the column is fed to a condenser, for example an evaporative cooler which is operated at about 80° to 180° C., in which only a proportion of the organic constituents and especially only a proportion of the naphthalene, is separated off in the liquid form. For example, about 10 to 90% of the naphthalene contained in the stream of gas can be separated off as a liquid in this way. Part of this liquefied napthalene, for example an amount of about 30 to 100% thereof, is then fed, as reflux, to the top of the column and/or part thereof, for example an amount of about 0 to 70%, is recycled to other points in the anthraquinone synthesis. The gas mixture which leaves the evaporative cooler and which generally still contains naphthalene and oxygen as well as, in some cases, nitrogen, steam and carbon dioxide, can then be fed, within the framework of the anthraquinone synthesis, to the feed product for the oxidation of naphthalene to naphthoquinone and phthalic anhydride.

The distillation system to be used according to the invention can be operated, for example, at temperatures from about 100° to 300° C., preferably about 150° to 250° C., and under normal pressure or elevated pressure, for example under about 1 to 20 bars and preferably under about 3 to 10 bars.

Materials which can be used for the distillation system to be used according to the invention and for its additional units are, for example, stainless steel. It is advantageous to provide the entire column with a steam-heated twin jacket.

The residence time of the naphthalene, phthalic anhydride and tetrahydroanthraquinone-anthraquinone within the distillation system can be choosen within wide limits and depends mainly from the temperature. At higher temperatures lower residence times are preferred and vice versa. For example, at temperatures in the range of about 150° to 250° C. the residence time is generally at least about 20 minutes and preferably at least about 40 minutes. Little is realized having it longer than about 100 minutes and even about 70 minutes since it will then unnecessarily tie up the apparatus, i.e. reduce its capacity, without significantly increasing the conversion or naphthalene recovery.

The process according to the invention has the advantage that it is possible, in one apparatus, to carry out the conversion of tetrahydroanthraquinone to anthraquinone, with good yields and high selectivities, and, at the same time, quantitatively or partially to separate off naphthalene. The heat of reaction from the reaction of tetrahydroanthraquinone to give anthraquinone can be utilized in order, by vaporizing liquid naphthalene, to obtain the gaseous naphthalene which is required in the first stage of the anthraquinone synthesis. Furthermore, it is possible, in the distillation system to be used according to the invention, for desirable side-reactions for the elimination of impurities contained in the feed stream, for example the conversion of phthalic acid to phthalic anhydride and water and the conversion of naphthoquinone to high-boiling compounds, to proceed. It is possible, if appropriate by adding phthalic anhydride to the feed material or to the distillation system, so to carry out the process according to the invention that the anthraquinone formed is obtained in the form of a solution in phthalic anhydride, which is very advantageous for continuous working up, for example by distillation.

The anthraquinone prepared according to the invention is an important intermediate product for the preparation of dyestuffs.

The process according to the invention is explained in more detail with the aid of the examples which follow, without being restricted thereto:

EXAMPLE 1

41 kg/hour of a liquid mixture having the following composition:
Naphthalene: 80.2% by weight
Tetrahydroanthraquinone: 7.5% by weight
Phthalic anhydride: 9.6% by weight
Naphthoquinone: 0.2% by weight
Phthalic acid: 0.2% by weight
Butadiene: 2.2% by weight
high-boiling compounds: 0.1% by weight
By-products (for example vinylcyclohexane and dihydroxy-naphthacenequinone): traces
are fed, at a temperature of 220° C., into a rectifying column. Together with this feed stream, a stream of 11 kg/hour of phthalic anhydride is fed into the column. The above-mentioned liquid mixture is introduced, together with the phthalic anhydride, into the column at the boundary between the rectifying section and the stripping section.

190 cubic meters (S.T.P.) per hour of a stream of gas having a composition of
Oxygen: 6.6% by volume
Water: 4.7% by volume
Carbon dioxide: 0.6% by volume
Carbon monoxide: 0.1% by volume
Naphthalene: 0.4% by volume
Nitrogen: 87.6% by volume
are fed into the lowest part of the vaporizer. The temperature of the stream of gas is 150° C.

The column has a diameter of 300 mm. The total height is 8.7 m without the vaporizer. The stripping section of the column consists of 11 sieve trays each of which is provided with 110 holes 6 mm in diameter; this gives a free cross-section of 4.4%. The sieve trays are all connected to one another by means of a downcomer of customary construction, so that the liquid level on the sieve trays adjusts to 60 mm. The residence time of the liquid on each tray is, accordingly, about 160 seconds.

The rectifying section has a height of 5.5 m and is filled with 25×25 mm packing. The packed height is about 3.2 m. The vaporizer of the column has a diameter of 462 mm and a height of 1,100 mm. A tube coil which is 13 m in length and has tube dimensions of 33.7 mm for the external diameter and 4.05 mm for the wall thickness is installed in this vaporizer. It is connected to steam under 30 bars. A vertical two-component nozzle, through which the abovementioned stream of gas flows as a jet into the vaporizer, is located centrally along the axis in the lowest part of the vaporizer. About 5 $m^3$/hour of a stream of liquid are taken off continuously from the vaporizer and fed via a centrifugal pump to the two-component nozzle. The entire column, including the vaporizer, is provided with a twin jacket, the interspace of which is connected to steam. The gases and vapors which leave the top of the column are fed to the lower part of a condenser which has an internal diameter of 340 mm and a height of 2,330 mm. A tube bundle consisting of 26 tubes having dimensions of 30 mm for the external diameter, 3.6 mm for the wall thickness and about 1,800 mm for the length is installed in this vertical cylinder. The outside of this tube bundle serves as a condensation surface. The heat of condensation is removed by water vaporizing inside the tube bundle. The steam is fed to a secondary condenser, which is located directly above the condenser for the product. The steam is condensed in this secondary condenser, which has a tube coil with a cooling area of about 0.6 $m^2$, and is recycled to the primary condenser. The uncondensed gases and vapors leave the upper part of the condenser; the condensed liquid, which is mainly naphthalene, is taken off at the lowest point and recycled via a reciprocating pump to the top of the column.

The operating conditions for this system are as follows:
Temperature at the top: 166° C.
Pressure at the top: 6.0 bars absolute
Sump temperature: 211° C.
Sump pressure: 6.4 bars absolute
Temperature in the condenser: 162° C.
Temperature in the secondary condenser: 152° C.
Steam pressure in the secondary condenser: 5 bars absolute The composition of the stream of gas which leaves the condenser in an amount of about 196 cubic meters (S.T.P.) per hour is:
Oxygen: 6.2% by volume
Water: 4.9% by volume
Carbon dioxide: 0.6% by volume
Carbon monoxide: 0.1% by volume
Naphthalene: 3.2% by volume
Nitrogen: 84.8% by volume
Butadiene: 0.2% by volume
Phthalic anhydride: traces
Vinylcyclohexene: traces The reflux of 10 kg/hour consists of approximately 100% by weight of naphthalene.

The composition of the stream of liquid which is taken off from the vaporiser in an amount of about 19 kg/hour is:
Naphthalene: 4.3% by weight
Phthalic anhydride: 75.4% by weight
Anthraquinone: 15.4% by weight
High-boiling compounds: 4.1% by weight
Phthalic acid: 0.5% by weight
Naphthoquinone: 0.3% by weight

EXAMPLE 2

38 kg/hour of a liquid mixture having the following composition:
Naphthalene: 73.8% by weight
Tetrahydroanthraquinone: 7.9% by weight
Phthalic anhydride: 15.5% by weight
Naphthoquinone: 0.2% by weight
Phthalic acid: 0.2% by weight
Butadiene: 2.3% by weight
High-boiling compounds: 0.1% by weight
By-products (for example vinylcyclohexane, and dihydroxy naphthacenequinone) traces are fed at a temperature of 220° C., together with a stream of 9 kg/hour of phthalic anhydride, uniformly to the three uppermost sieve trays in the rectifying column described in Example 1. The sieve trays are each connected by means of a downcomer of customary construction, so that the "dry" liquid level adjusts to 20, 30, 40 and 50 mm respectively on the first, second, third and fourth sieve tray from the top. The "dry" liquid level for the other trays is 60 mm. The other data relating to the construction of the system correspond to those of Example 1.

155 cubic meters (S.T.P.) per hour of a stream of gas having a composition of
Oxygen: 8.0% by volume
Nitrogen: 92.0% by volume
are fed into the lowest part of the column of the vaporizer. The temperature of the stream of gas is 150° C. The average residence time of the liquid per tray is about 130 seconds.

The operating conditions are as follows:
Temperature at the top: 166° C.
Pressure at the top: 6.0 bars absolute
Sump temperature: 211° C.
Sump pressure: 6.4 bars absolute
Temperature in the condenser: 162° C.
Temperature in the secondary condenser: 152° C.
Steam pressure in the secondary condenser: 5 bars absolute The composition of the stream of gas which leaves the condenser in an amount of about 161 cubic meters (S.T.P.) per hour is:
Oxygen: 7.5% by volume
Water: 0.4% by volume
Naphthalene: 3.0% by volume
Nitrogen: 88.8% by volume
Butadiene: 0.2% by volume
Phthalic anhydride: traces
Vinylcyclohexene: traces The reflux of 10 kg/hour consists of 100% by weight of naphthalene.

The composition of the stream of liquid which is taken off from the vaporizer in an amount of about 19 kg/hour is:
Naphthalene: 3.3% by weight
Phthalic anhydride: 77.2% by weight
Anthraquinone: 16.2% by weight
High-boiling compounds: 2.5% by weight Phthalic acid: 0.5% by weight
Naphthoquinone: 0.3% by weight

EXAMPLE 3

A distillation system which consists of a co-current bubble column with 3 chambers (reaction apparatus) and in which a column section is fitted on top of the bubble column is used.

The reaction apparatus has a height of 1,800 mm and a diameter of 300 mm. It is divided into 3 chambers which are separated from one another by perforated trays. The height of the chambers is 500 mm. In the uppermost chamber a level of 500 mm is ensured by an overflow into an external degasing vessel. The overflow at the same time ensures that the degasing vessel, which has a height of 800 mm and a diameter of 200 mm, is vented. The gas flows upwards through a sieve tray, which has 73 bores 5 mm in diameter, into the first chamber. The stream of liquid is fed in from the side. The partition trays below the second and third chambers are designed as multi-hole trays with 12 bores 10 mm in diameter. The three chambers each have a separate twin jacket, the interspace of which is connected to steam controllable at 30 bars. The overflow tube and the storage vessel are also provided with a twin jacket. They are connected to the same steam pressure control as the uppermost chamber of the reactor.

The column section has a total height of 13.08 m and a diameter of 300 mm. Working from bottom to top, the column section has the following inserts: after 2,700 mm without inserts there are 5 trays which each have 5 bores 28 mm in diameter. These trays do not have a definite liquid level. They are followed by 10 valve trays which each have 4 valves 28 mm in diameter. The liquid level on the trays adjusts to 60 mm. The downflow is effected through a downcomer of customary construction. A take-off weir is fitted below the lowest valve tray. A packed bed 2,700 mm in height is installed in the uppermost section. The entire column section is provided with a twin jacket which can be heated with steam.

The gases and vapors which leave the top of the column are fed to the lower part of a condenser which has an internal diameter of 340 mm and a height of 2,330 mm. A tube bundle consisting of 26 tubes having dimensions of 30 mm for the external diameter, 3.6 mm for the wall thickness and about 1,800 mm for the length is installed in this vertical cylinder. The outside of this tube bundle serves as a condensation surface. The heat of condensation is removed by water vaporizing inside the tube bundle. The steam is fed to a secondary condenser, which is located directly above the condenser for the product. The steam is condensed in this secondary condenser, which has a tube coil with a cooling area of about 0.6 m$^2$, and is recycled to the primary condenser. The uncondensed gases and vapors leave the upper part of the condenser; the condensed liquid, which is mainly naphthalene, is taken off at the lowest point and recycled via a reciprocating pump to the top of the column.

The distillation system is operated under the following operating conditions:
Temperature at the top: 154° C.
Pressure at the top: 5.7 bars
Condensation temperature: 132° C.
Sump temperature:
1st chamber: 185° C.
2nd chamber: 195° C.
3rd chamber: 205° C.
Sump pressure: 5.9 bars
56.6 kg/hour of a liquid mixture of the following composition:
Naphthalene: 82.95% by weight
Phthalic anhydride: 6.0% by weight
Tetrahydroanthraquinone: 8.4% by weight
Naphthoquinone: 0.85% by weight
High-boiling compounds: 0.8% by weight
Butadiene: 1.0% by weight
By-products: traces
are fed to the lowest chamber.

The inlet temperature is 180° C. At the same time, a stream of 20.9 kg/hour of phthalic anhydride is fed at the same temperature into the same chamber.

The stream, of 100 cubic meters (S.T.P.) of gas which is fed into the lowest chamber of the bubble column has a temperature of 180° C. and the following composition:
$N_2$: 78.5% by volume
$O_2$: 4.0% by volume
$CO_2$: 10.0% by volume
$H_2O$: 7.2% by volume
Naphthalene: 0.3% by volume
By-products: traces About 102 cubic meters (S.T.P.) of gas having the composition:
$N_2$: 77.4% by volume
$O_2$: 3.0% by volume
$CO_2$: 10.0% by volume
$H_2O$: 8.0% by volume
Naphthalene: 1.4% by volume
Butadiene: 0.2% by volume
By-products: traces
leave the condenser. The reflux of 10 kg/hour consists of 100% by weight of naphthalene. The stream, of 71 kg/hour, of liquid which is withdrawn from the storage vessel has the following composition:
Naphthalene: 55.9% by weight
Phthalic anhydride: 34.0% by weight
Anthraquinone: 6.6% by weight
Tetrahydroanthraquinone: 0.1% by weight
High-boiling compounds: 3.4% by weight
By-products: traces It will be appreciated that the instant specification and examples are set forth by way of illustration and not limitation, and that various modifications and changes may be made without departing from the spirit and scope of the present invention.

What is claimed is:

1. In a process for the preparation of anthraquinone by reacting a liquid feed containing naphthalene, phthalic anhydride and tetrahydroanthraquinone with oxygen at elevated temperature while simultaneously separating off at least part of the naphthalene, in a distillation system which consists of a column having a rectifying section and a boiler, the improvement wherein the boiler of the distillation system has several chambers and is operated as a cascade and the liquid feed containing naphthalene, phthalic anhydride and tetrahydroanthraquinone is fed only into the lowest chamber of the boiler.

2. The process according to claim 1, wherein the chambers are arranged above one another.

3. The process according to claim 1, wherein the chambers are arranged alongside one another.

4. The process according to claim 1, wherein the chambers are arranged in the form of a kettle cascade and the final kettle is the sump of the column.

5. The process according to claim 1, wherein the rectifying section of the column has 2 to about 20 theoretical plates and contains packing, sieve trays, bubble cap trays, valve trays or drip trays.

6. The process according to claim 1, wherein the addition of oxygen is effected at at least one point in the lower region of the distillation system.

7. The process according to claim 1, wherein a two-component nozzle is used for the addition of the oxygen.

8. The process according to claim 7, wherein about 3 to 200 kg of liquid per $m^3$ actual of gas are fed to the two-component nozzle.

9. The process according to claim 1, wherein a liquid mixture consisting essentially of residual naphthalene, phthalic anhydride and anthraquinone is taken off from the final boiler chamber of the column, and a stream of gas which contains the unconverted proportions of the gas fed into the lower part of the column, as well as naphthalene, is taken off at the top of the column.

10. The process according to claim 9, wherein the stream of gas taken off at the top of the column is subjected to cooling thereby condensing and separating organic constituents in solid or liquid form from this gas.

11. The process according to claim 10, wherein only a proportion of the organic constituents is separated off by means of an evaporative cooler and the gas mixture which leaves the cooler is recycled as feed material for the oxidation of napthalene to naphthoquinone and phthalic anhydride.

12. The process according to claim 7, wherein a liquid mixture is taken off from the boiler, some of the liquid mixture which is taken off is fed through a heat exchanger and this stream is fed to the two-component nozzle.

* * * * *